(12) United States Patent
Rousseau

(10) Patent No.: US 6,800,082 B2
(45) Date of Patent: Oct. 5, 2004

(54) ABSORBABLE MESH DEVICE

(75) Inventor: Robert A. Rousseau, Ottsville, PA (US)

(73) Assignee: Ethicon, Inc., Somerville, NJ (US)

( * ) Notice: Subject to any disclaimer, the term of this patent is extended or adjusted under 35 U.S.C. 154(b) by 54 days.

(21) Appl. No.: 10/007,163

(22) Filed: Oct. 19, 2001

(65) Prior Publication Data

US 2003/0078602 A1 Apr. 24, 2003

(51) Int. Cl.$^7$ .............................................. A61B 17/04
(52) U.S. Cl. .................................................... 606/151
(58) Field of Search ........................................ 606/151

(56) References Cited

U.S. PATENT DOCUMENTS

| | | | |
|---|---|---|---|
| 4,520,821 A | 6/1985 | Schmidt et al. ............. | 606/151 |
| 4,633,873 A | 1/1987 | Dumican et al. ............ | 606/151 |
| 4,838,884 A | 6/1989 | Dumican et al. ............ | 606/151 |
| 4,865,031 A | 9/1989 | O'Keeffe | |
| 4,871,365 A | 10/1989 | Dumican ..................... | 606/151 |
| 5,002,551 A | 3/1991 | Linsky et al. ............... | 606/151 |
| 5,007,916 A | 4/1991 | Linsky et al. ............... | 606/151 |
| 5,092,884 A | 3/1992 | Devereux et al. ........... | 606/151 |
| 5,634,931 A | 6/1997 | Kugel .......................... | 606/151 |
| 5,686,090 A | 11/1997 | Schilder et al. ............. | 606/151 |
| 5,769,864 A | 6/1998 | Kugel .......................... | 606/151 |
| 5,795,584 A | 8/1998 | Totakura et al. ............. | 606/151 |
| 5,916,225 A | 6/1999 | Kugel .......................... | 606/151 |
| D416,327 S | 11/1999 | Kugel .......................... | 606/151 |
| 6,171,318 B1 | 1/2001 | Kugel et al. ................. | 606/151 |
| 6,174,320 B1 | 1/2001 | Kugel et al. ................. | 606/151 |
| 6,176,863 B1 | 1/2001 | Kugel et al. ................. | 606/151 |
| 6,224,616 B1 | 5/2001 | Kugel .......................... | 606/151 |

FOREIGN PATENT DOCUMENTS

| | | | |
|---|---|---|---|
| EP | 0303496 | 2/1989 | |
| EP | 0334046 | 9/1989 | |
| EP | 0560934 | 9/1993 | |
| EP | 610731 A1 * | 8/1994 | ........... A61L/31/00 |
| WO | 9906079 | 2/1999 | |
| WO | 9906080 | 2/1999 | |
| WO | 9951163 | 10/1999 | |

OTHER PUBLICATIONS

European Search Report dated Dec. 11, 2003 for corresponding Appln. No. EP 02257248.

* cited by examiner

Primary Examiner—Gary Jackson

(57) ABSTRACT

A hernia repair device, which is implantable in a patient's body, includes first and second layers cooperating with one another so as to form an implantable patch for repairing a hernia defect. The first layer is made from a textile material which is absorbable in a patient's body, while the second layer is made from a non-absorbable textile material. When the patch is implanted in a patient's body, the non-absorbable second layer remains permanently implanted, while the absorbable first layer is dissolved.

20 Claims, 4 Drawing Sheets

ABSORBABLE MESH DEVICE

FIELD OF THE INVENTION

The present invention relates to a hernia repair device and, more specifically, to a hernia patch used to repair damaged tissue or muscle walls.

BACKGROUND OF THE INVENTION

Mesh-type patches have been used to repair hernia defects (e.g., openings or holes formed in a wall of an organ, through which interior organs tend to protrude). Typically, these patches are permanently implanted in a patient's body and may hence cause postoperative discomfort to the patient.

U.S. Pat. No. 6,224,616 B1 discloses a mesh-type patch for repairing an abdominal wall hernia. More particularly, the patch is formed by top and bottom layers made from an inert mesh material. An implantable loop is positioned between the top and bottom layers to keep the patch expanded under tension in a planar configuration. In order to repair a hernia defect, the entire patch is implanted permanently in a patient's body. Because the total mass or weight of the implanted patch is relatively large and because the patch is rigid, it tends to be noncompliant with respect to the natural anatomy of the patient and increases the risk of seroma formation and/or recurrence. Moreover, the permanent tension induced by the implantable loop may cause additional discomfort to the patient.

In the foregoing circumstances, there is a need for a hernia patch that has a reduced mass, that is substantially tension-free and/or that otherwise overcomes the disadvantages and shortcomings of the hernia patches discussed above.

SUMMARY OF THE INVENTION

The present invention overcomes the disadvantages and shortcomings of the prior art discussed above by providing a hernia repair device implantable in a patient's body. More particularly, the hernia repair device includes first and second layers cooperating with one another so as to form an implantable patch for repairing a hernia defect. The first layer is made from a textile material which is absorbable in a patient's body, while the second layer is made from a non-absorbable textile material. When the patch is implanted in a patient's body, the non-absorbable second layer remains permanently implanted, while the absorbable first layer is dissolved.

In accordance with one embodiment, the device includes a third layer, which is attached to the first layer so as to form a pouch for receiving the second layer therein. The third layer is made from an absorbable textile material such that when the patch is implanted in a patient's body, the absorbable third layer is dissolved.

Other features and aspects of the present invention will become more fully apparent from the following detailed description of the exemplary embodiment.

BRIEF DESCRIPTION OF THE DRAWINGS

For a more complete understanding of the present invention, reference is made to the following detailed description of the exemplary embodiment considered in conjunction with the accompanying drawings, in which.

DETAILED DESCRIPTION OF THE EXEMPLARY EMBODIMENT

Figure 1:
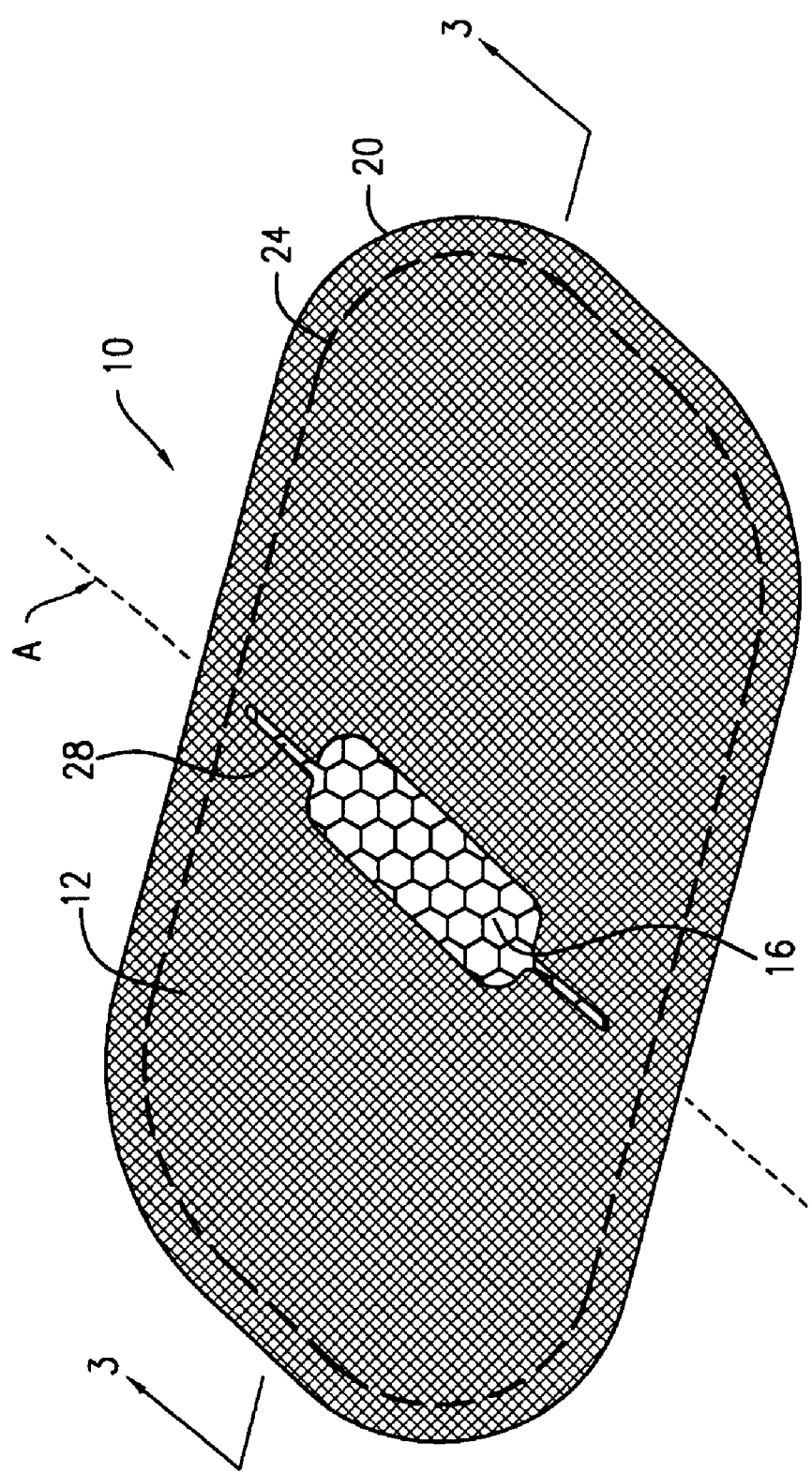
FIG. 1 is a perspective view of a hernia patch constructed in accordance with the present invention.
Figure 2:
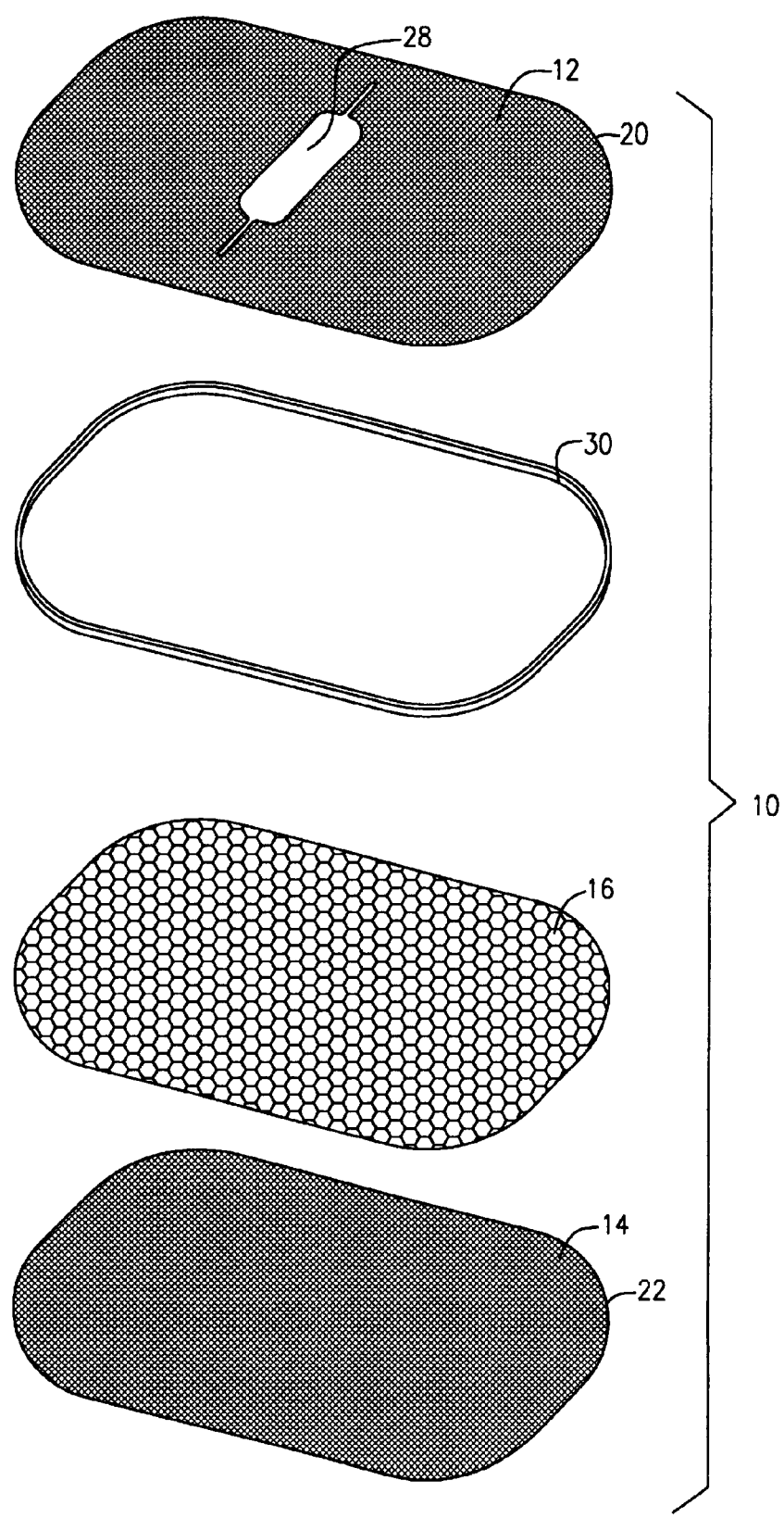
FIG. 2 is an exploded, perspective view of the hernia patch shown in FIG. 1.

FIGS. 1 and 2 show a hernia patch 10 constructed in accordance with the present invention. The hernia patch 10 includes a top layer 12 and a bottom layer 14 attached to one another so as to form a pouch 15 (see FIG. 3) therebetween. Each of the top and bottom layers 12, 14 is made from an absorbable medical textile material that can be absorbed (i.e., dissolve or disintegrate) in or into a patient's body upon implantation (e.g., polyglactin meshes, such as those marketed by Johnson & Johnson under the trademark "VICRYL"). In this manner, the top and bottom layers 12, 14 can be absorbed (i.e., dissolve or disintegrate) in a patient's body when the hernia patch 10 is implanted into same.

Figure 4:
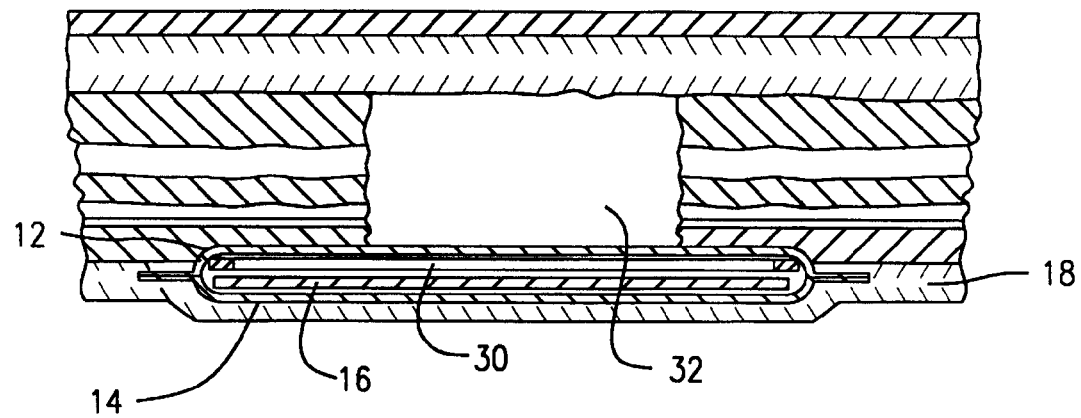
FIGS. 4 and 5 are schematic views illustrating the operation of the hernia patch shown in FIG. 1.

The hernia patch 10 also has an inert layer 16 located in the pouch 15 between the top and bottom layers 12, 14. More particularly, the inert layer 16 is made from a synthetic non-absorbable medical textile material (e.g., polypropylene meshes, such as those marketed by Johnson & Johnson under the trademark "PROLENE") so as to remain permanently in a patient's body after implantation. The top and bottom layers 12, 14 and the inert layer 16 are sized and shaped so as to extend across a hernia defect 18 (see FIG. 4). In this regard, the top and bottom layers 12, 14 and the inert layer 16 have a substantially oval shape. The top and bottom layers 12, 14 and the inert layer 16 are also flexible such that the hernia patch 10 assumes a substantially planar configuration when it is expanded and assumes a collapsed configuration when it is folded generally about its lateral axis A (see FIG. 1). In this manner, the hernia patch 10 can be delivered to the hernia defect 18 in its collapsed configuration and then expanded into its planar configuration for repairing the hernia defect 18, as will be discussed in greater detail hereinafter.

Figure 3:
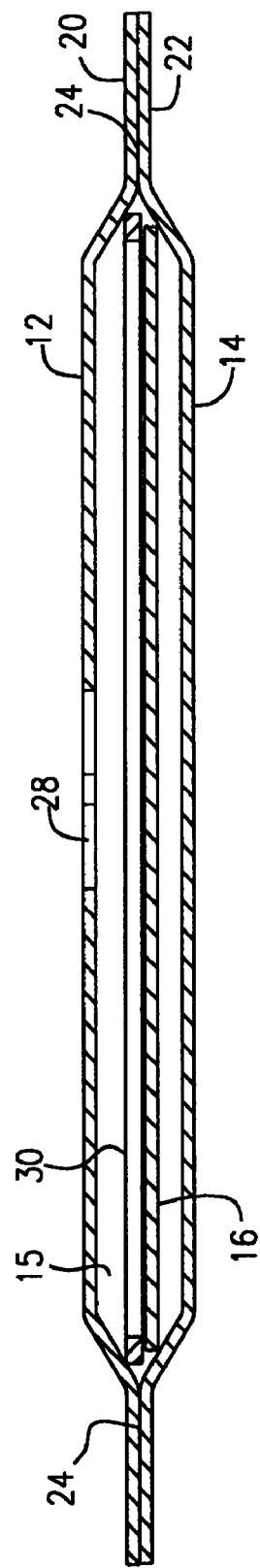
FIG. 3 is a cross-sectional view of the hernia patch shown in FIG. 1, taken along section lines 3—3 and looking in the direction of the arrows.

With reference to FIG. 3, the top and bottom layers 12, 14 have outer edges 20, 22, respectively. The outer edge 22 of the bottom layer 14 is secured to the outer edge 20 of the top layer 12 by a conventional attaching method (e.g., stitching, ultrasonic bonding, radio frequency bonding, heat bonding or solvent bonding), thereby forming the pouch 15, which is provided with an interior hollow. More particularly, the top and bottom layers 12, 14 are attached to one another such that a seam 24 (see FIGS. 1 and 3) is formed at any suitable distance from the outer edges 20, 22. For instance, the seam 24 can be formed from the outer edges 20, 22 at a distance ranging from about 0.5 cm to about 1.5 cm.

Still referring to FIG. 3, the pouch 15 is sized and shaped so as to receive the inert layer 16 therein. The inert layer 16 is freely contained in the pouch 15 (i.e., it is not bonded or attached to the top layer 12 or the bottom layer 14). Alternatively, the inert layer 16 can be attached to one or both of the top and bottom layers 12, 14.

Referring back to FIGS. 1 and 2, the top layer 12 has a lateral slit 28 formed therein. The slit 28 is sized and shaped such that a finger or fingers of a person (e.g. surgeon) can be inserted into the pouch 15 through the slit 28 for purposes to be discussed hereinbelow. The slit 28 extends in a direction substantially parallel to the lateral axis A of the top layer 12.

A resilient spring 30 (see FIGS. 2 and 3) is positioned in the pouch 15 between the top layer 12 and the inert layer 16.

More particularly, the spring 30, which is provided with a ring shape, has an outer radius slightly greater than that of the seam 24 for expanding the hernia patch 10 into its planar configuration. The spring 30 is preferably made from a flexible absorbable polymer (e.g., polydioxanone polymers, such as the polymers marketed by Johnson & Johnson under the trademark "PDS", or polymers containing lactides, glycolides, polyglactin, etc.) such that the spring 30 can be absorbed (i.e., dissolve or disintegrate) in a patient's body after implantation. Alternatively, the spring 30 can be eliminated or replaced by conventional or other urging mechanisms.

In order to implant the hernia patch 10 in a patient's body, an incision is made above the location of the hernia defect 18. A hernia sac (not shown) is dissected and/or ligated through the incision so as to form an opening 32 for inserting the hernia patch 10 therethrough. One or more fingers of a surgeon is inserted into the pouch 15 through the slit 28. With the fingers inserted into the pouch 15, the hernia patch 10 is folded generally about its lateral axis A so as to orient same in its collapsed configuration. The hernia patch 10 is then delivered to the hernia defect 18 in its collapsed configuration. Next, the hernia patch 10 is unfolded (i.e., expanded) by the fingers of the surgeon so as to orient same in its planar configuration (see FIG. 4). After the hernia patch 10 is expanded into its planar configuration and properly placed in the hernia defect 18, the incision is closed.

Figure 5:
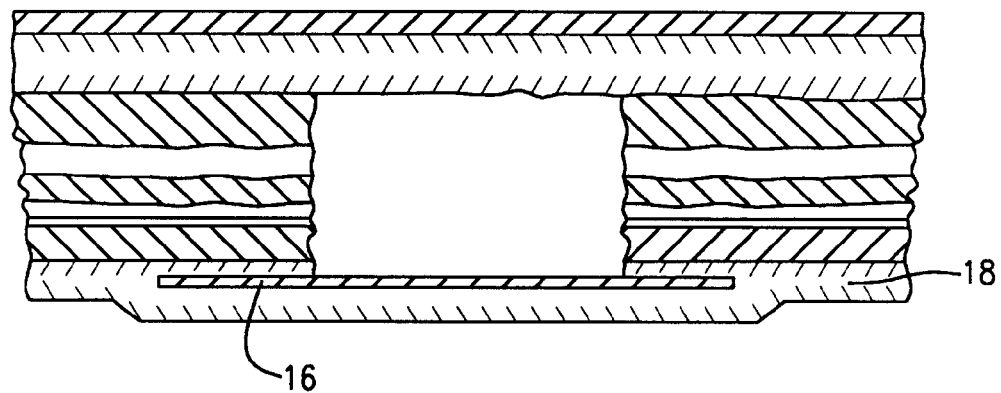

After the implantation of the hernia patch 10 in the patient's body, the top and bottom layers 12, 14 stimulate tissues surrounding the hernia defect 18, facilitating scar tissue in-growth into the hernia patch 10. After the lapse of a predetermined time period (e.g., approximately fifty to ninety days), the top and bottom layers 12, 14 and the spring 30 are absorbed (i.e., dissolve or disintegrate) in the patient's body. As a result, only the inert layer 16 remains permanently in the patient's body as a patch for repairing and/or reinforcing the hernia defect 18 (see FIG. 5). In other words, the top and bottom layers 12, 14 are used as a temporary deployment vehicle for placing the inert layer 16 at the site of the hernia defect 18.

It should be appreciated that the present invention provides numerous advantages over the conventional hernia repair devices discussed above. For instance, because the top and bottom layers 12, 14 and the spring 30 are constructed so as to be absorbed in a patient's body, a significant reduction in the mass (i.e., weight) of the hernia patch 10 can be obtained. In addition, because the spring 30 does not remain permanently in the patient's body, a substantially tension-free repair of the hernia defect 18 can be performed. As a result, the compliance of the integrated mesh is improved with the use of the hernia patch 10. The hernia patch 10 is also simple to implant into a patient's body. Studies have shown that the "VICRYL" mesh is non-antigenic and non-pyrogenic.

It should be noted that the hernia patch 10 can have numerous modifications and variations. For instance, the top and bottom layers 12, 14 can be made from any type of absorbable, biocompatible material. Moreover, only one or a portion of the top and bottom layers 12, 14 can be made from an absorbable, biocompatible material. Likewise, the inert layer 16 can be made from any type of non-absorbable, biocompatible material. Further, while the spring 30 is preferably made from a polydioxanone polymer, it can be made from other types of absorbable polymers or can be made from a non-absorbable material. In addition, the hernia patch 10 is suitable for repairing hernias having different sizes and shapes and can be anchored beyond the edge of the hernia defect 18 with sufficient rigidity so as to prevent migration or sliding of the hernia patch 10. The hernia patch 10 can also be used to prevent or to repair many different types of abdominal hernias, such as inguinal hernias, femoral hernias, incisional hernias and umbilical hernias, etc., whether or not the hernias are direct or indirect. In addition, the top and bottom layers 12, 14 and the inert layer 16 can have different shapes (e.g., circular, square, polygonal, etc.). If the spring 30 is employed, it can be positioned in a different location (e.g., between the inert layer 16 and the bottom layer 14).

It will be understood that the embodiment described herein is merely exemplary and that a person skilled in the art may make many variations and modifications without departing from the spirit and scope of the invention. All such variations and modifications, including those discussed above, are intended to be included within the scope of the invention as defined in the appended claims.

I claim:

1. A hernia repair device implantable in a patient's body, comprising a first layer; a second layer cooperating with said first layer so as to form an implantable patch for repairing a hernia defect, at least one portion of said first layer being made from a textile material which is absorbable in a patient's body, and at least one portion of said second layer being made from a non-absorbable textile material; and a third layer, said first and third layers being attached to one another so as to form a pouch for receiving said second layer therein, whereby when said patch is implanted in a patient's body, said at least one portion of said second layer remains permanently implanted, while said at least one portion of said first layer is absorbed.

2. The hernia repair device of claim 1, further comprising expanding means for expanding said patch into its planar configuration, said expanding means being made from a second absorbable material so as to be absorbed when said patch is implanted in a patient's body.

3. The hernia repair device of claim 2, wherein said expanding means a spring located in said pouch.

4. The hernia repair device of claim 1, wherein said third layer cooperates with said first layer and said second layer to form said patch.

5. The hernia repair device of claim 1, wherein said second layer is contained in said pouch without being attached to any one of said first and third layers.

6. A hernia repair device comprising a first layer; a second layer cooperating with said first layer so as to form an implantable patch for repairing a hernia defect, at least one portion of said first layer being made from a textile material which is absorbable in a patient's body, and at least one portion of said second layer being made from a non-absorbable textile material; and a third layer, said first and third layers being attached to one another so as to form a pouch for receiving said second layer therein, at least one portion of said third layer being made from said absorbable textile material, whereby when said patch is implanted in a patient's body, said at least one portion of said second layer remains permanently implanted, while said at least one portion of said first layer and said at least one portion of said third layer are absorbed.

7. The hernia repair device of claim 6, wherein said first and third layers are made in their entirety from said absorbable textile material.

8. The hernia repair device of claim 7, further comprising expanding means for expanding said patch into its planar configuration, said expanding means being made from a second absorbable material so as to be absorbed when said patch is implanted in a patient's body.

9. The hernia repair device of claim 8, wherein said expanding means includes a spring located in said pouch.

10. The hernia repair device of claim 9, wherein said third layer cooperates with said first layer and said second layer to form said patch.

11. The hernia repair device of claim 10, wherein said absorbable textile material is polyglactin.

12. The hernia repair device of claim 11, wherein said second absorbable material is polydioxanone.

13. The hernia repair device of claim 12, wherein said non-absorbable material is polypropylene.

14. The hernia repair device of claim 13, further comprising receiving means, in communication with said pouch, for receiving at least one finger of a person.

15. The hernia repair device of claim 14, wherein said receiving means includes a slit formed in one of said first and third layers.

16. The hernia repair device of claim 6, wherein said second layer is contained in said pouch without being attached to any one of said first and third layers.

17. The hernia repair device of claim 6, wherein said at least one portion of said first layer and said at least one portion of said third layer are made from a material so as to be completely absorbed in a patient's body within a certain period of time.

18. The hernia repair device of claim 17, wherein said period of time is in a range from about fifty days to about ninety days.

19. The hernia repair device of claim 6, wherein said absorbable textile material is polyglactin.

20. The hernia repair device of claim 6, wherein said nonabsorbable textile material is polypropylene.

* * * * *